US007499813B2

(12) United States Patent
Yamamoto et al.

(10) Patent No.: US 7,499,813 B2
(45) Date of Patent: Mar. 3, 2009

(54) DEVICE AND METHOD FOR INSPECTING FOR FLAW ON SURFACE OF WORK

(75) Inventors: Makoto Yamamoto, Komatsu (JP); Akihiro Yoshimoto, Komatsu (JP)

(73) Assignee: Komatsu Machinery Corporation, Ishikawa (JP)

( * ) Notice: Subject to any disclaimer, the term of this patent is extended or adjusted under 35 U.S.C. 154(b) by 0 days.

(21) Appl. No.: 11/659,737

(22) PCT Filed: Aug. 25, 2005

(86) PCT No.: PCT/JP2005/015461

§ 371 (c)(1), (2), (4) Date: Feb. 8, 2007

(87) PCT Pub. No.: WO2006/025257

PCT Pub. Date: Mar. 9, 2006

(65) Prior Publication Data

US 2008/0033664 A1    Feb. 7, 2008

(30) Foreign Application Priority Data

Sep. 3, 2004    (JP) .............................. 2004-256776

(51) Int. Cl.
G01B 5/28    (2006.01)
(52) U.S. Cl. ...................................................... 702/35
(58) Field of Classification Search .................. 702/35, 702/36, 39, 57, 59, 66, 70, 71, 73, 75, 149, 702/151, 159, 168, 183, 185; 73/618, 627, 73/652; 250/310
See application file for complete search history.

(56) References Cited

U.S. PATENT DOCUMENTS

| 4,385,699 | A | * | 5/1983 | Ashina ........................ 209/538 |
| 4,598,998 | A | * | 7/1986 | Kamei et al. .............. 356/237.5 |
| 5,005,417 | A | * | 4/1991 | Kawasaki et al. .............. 73/593 |
| 5,508,944 | A |   | 4/1996 | Danielli |
| 5,532,591 | A | * | 7/1996 | Logue ......................... 324/242 |
| 5,936,726 | A | * | 8/1999 | Takeda et al. ............. 356/237.2 |
| 6,256,897 | B1|   | 7/2001 | Mikame |
| 6,550,333 | B1| * | 4/2003 | Kiuchi ......................... 73/593 |

(Continued)

FOREIGN PATENT DOCUMENTS

JP    A6-265334    9/1994

(Continued)

*Primary Examiner*—Edward Raymond
*Assistant Examiner*—Mohamed Charioui
(74) *Attorney, Agent, or Firm*—Posz Law Group, PLC (57) ABSTRACT

A device for inspecting for minute flaws upon the outer surface of journal or pin portions of a crank shaft comprises a main device 12 and a control device 14. The main device 12 brings a gauge head 56, which can freely move forwards and backwards along a Y axis direction, into contact with an inspection region 16A of the the crank shaft 16 while rotating the crank shaft 16 around a rotational axis 16C, measures the surface position of the inspection region 16A for each of rotational angles, and obtains surface portion waveform data corresponding to rotational angle. The gauge head 56 has an oscillation function, and always contacts against the inspection region 16A during rotation. The control device 14 extracts high frequency waveform components from the obtained waveform data, and detects flaws on the inspection region based on the high frequency waveform components.

17 Claims, 10 Drawing Sheets

U.S. PATENT DOCUMENTS 6,588,278 B1 * 7/2003 Takishita et al. .............. 73/618

FOREIGN PATENT DOCUMENTS

| JP | 7-55494 Y2 | 12/1995 |
| JP | A10-177326 | 6/1998 |
| JP | 11-083413 | 3/1999 |
| JP | A11-271008 | 10/1999 |
| JP | A-2004-069410 | 3/2004 |

* cited by examiner

DEVICE AND METHOD FOR INSPECTING FOR FLAW ON SURFACE OF WORK

TECHNICAL FIELD

The present invention relates to a device and a method for inspecting for the presence of flaws upon the surface of a workpiece, and more particularly relates, for example, to an appropriate device and method for inspecting for flaws upon the surface of a journal portion or a pin portion of a crank shaft, upon the surface of the cam portion of a cam shaft, or the like.

BACKGROUND ART

With a processed manufactured product like a crank shaft or a cam shaft or the like, sometimes convex flaws such as traces of blows during processing are present at locations such as journal portions, pin portions, cam portions or the like at which high accuracy surface processing has been performed. It is necessary reliably to discover and to eliminate manufactured products upon which such flaws are present by inspecting them. Thus, in the prior art, testing by visual inspection has been performed upon all the products by hand.

Now, in Japanese Laid-Open Patent Publication Heisei 11-83413, there is disclosed a device which automatically measures the diameter, the roundness, the straightness, and the like of a journal portion or a pin portion by, in a state in which a contactor which can shift in the direction vertical to the rotational axis of a crank shaft is contacted with a constant force against the outer circumferential surface of the journal portion or the pin portion of the crank shaft, measuring the displacement of this contactor in each angular rotational position while rotating the crank shaft.

SUMMARY

Inspecting of all the products by visual inspection by hand entails routine and distressing labor for the inspection personnel, and moreover increases the cost of manufacture. Thus, it is desirable to develop a technique for detecting flaws automatically. As a method for such automatic detection, it may be contemplated to measure the external diameter of the manufactured product by using the measurement device disclosed in Japanese Laid-Open Patent Publication Heisei 11-83413. However, since the flaws which it is desired to detect are minute ones which cannot easily be discovered except on the part of experienced inspection personnel, accordingly, if even a slight error is included in the result of measuring an external diameter, this error makes the detection of flaws difficult. For example, it is necessary to eliminate errors such as the following.

(1) The cross sectional shape of the inspection region upon the workpiece (such as, for example, the journal portion or the pin portion of a crank shaft, or the cam portion of a cam shaft or the like) is not necessarily absolutely perfectly circular, and sometimes is slightly distorted. With a cam portion, this is all the more the case. A technique is needed for automatically eliminating measurement errors due to such deformation from a perfectly circular cross sectional shape.

(2) The surface at the inspection region is not necessarily perfectly perpendicular to the rotational axis of the workpiece, and sometimes is slightly inclined with respect thereto. A technique is needed for automatically eliminating measurement errors due to such inclination from the perpendicular.

(3) The contact surface of the detector against the workpiece is not necessarily perfectly planar, and sometimes minute concavities or convexities are present thereupon. A technique is needed for automatically eliminating measurement errors due to such concavities and convexities.

(4) The contact surface of the detector against the workpiece is not necessarily perfectly perpendicular to the rotational axis of the workpiece, and sometimes is slightly inclined with respect thereto. A technique is needed for automatically eliminating measurement errors due to such inclination from the perpendicular.

(5) An encoder is used for measuring the angular rotational position of the workpiece. However, the pitch of such an encoder is not necessarily accurately constant, and sometimes includes a slight error. A technique is needed for automatically eliminating measurement errors due to such pitch errors.

Accordingly, the object of the present invention is to make it possible to inspect for the presence of minute flaws upon a workpiece surface automatically.

According to the present invention, a flaw inspection device which inspects for the presence of flaws on the surface of a workpiece includes: a surface position measurement means which, while rotating the workpiece around a predetermined rotational axis, measures the surface position of an inspection region of the workpiece in a direction perpendicular to the rotational axis, for each rotational angle; a surface waveform acquisition means which receives the output signal of the surface position measurement means, and acquires surface waveform data which specifies the surface position with respect to rotational angle; a high frequency waveform extraction means which extracts, from the surface waveform data, high frequency waveform data which has a frequency higher than a predetermined frequency, or high frequency waveform data which specifies a change of a position within an angular range smaller than a predetermined angle; and a flaw decision means which decides upon the presence or absence of a flaw at the inspection region, based upon the high frequency waveform data which has been extracted.

In a preferred embodiment, the surface position measurement means includes a gauge head which contacts against the surface of an inspection region upon the workpiece. And since the gauge head, along with shifting freely along a first direction which is orthogonal to the rotational axis of the workpiece, is also biased in the direction towards the workpiece, accordingly it continuously contacts against the inspection region of the workpiece while the workpiece is rotated. Moreover, by measuring the position of the gauge head for each rotational angle while the workpiece is rotated, the surface position of the inspection region is measured for each rotational angle. The contacting surface of the gauge head to the inspection region has some length in a direction which is orthogonal to the shifting direction of the gauge head and to the direction of the rotational axis of the workpiece, and this length is greater than or equal to the stroke length of the inspection region in that direction when the workpiece rotates. Due to this, the gauge head is always contacted against the inspection region of the workpiece while the workpiece is being rotated. Furthermore, the contacting surface of the gauge head to the inspection region is a plane which has been processed to an accuracy equal to or greater than that of the surface of the inspection region of the workpiece, and moreover has a width in the direction of the rotational axis which almost corresponds to the width of the inspection region upon the workpiece in the same direction. By rotating the workpiece once, wherever a flaw may be upon the surface of the inspection region, it is possible to detect it, since the gauge head is in contact with the entire area of the surface of the inspection region.

Or, it would also be acceptable for the contacting surface of the gauge head to the inspection region to have a width which almost corresponds to the minimum width among the widths which correspond to the straight line portions of the inspection regions in the direction of the rotational axis. And, by shifting the gauge head through just a distance less than or equal to the width of this contacting surface along the rotational axis direction each time the workpiece rotates once, it is possible to be able to detect flaws in cylindrical surfaces of many different types of width, with a single gauge head of one width.

In a preferred embodiment, the gauge head described above is made to be capable of swinging over a predetermined angular range around, as a center, a rotational axis in a direction which is orthogonal to the direction of the rotational axis of the workpiece and to the shift direction of the gauge head. Due to this swing function, it is possible appropriately to contact the contacting surface of the gauge head against the surface of the inspection region, irrespective of any parallelism error of the contacting surface of the gauge head with respect to the surface of the inspection region.

In a preferred embodiment, based upon the high frequency waveform data, the above described flaw decision means obtains the rate of change (the gradient) with respect to rotational angle of the surface position of the inspection region, and/or the height or the width or the like of portions at which the surface position changes with respect to rotational angle, and detects flawing in the inspection region by comparing these with a threshold value set in advance.

And, in a preferred embodiment, there are provided a plurality of contour measurement units whose relative positions with respect to the workpiece are variable, and these contour measurement units simultaneously measure the surface positions of different inspection regions upon the same workpiece independently. Due to this, it is possible to complete the inspecting of all of the inspection regions within a short time period, and moreover it is possible to perform the inspecting flexibly, even for different types of workpiece. For example, if inspecting of a four cylinder crank shaft is to be performed at a total of ten spots, i.e. four spots upon pins, five spots upon journals, and one spot upon a flange, then the inspecting may be performed at these ten spots while rotating the workpiece three times, by using four surface position measurement means. By doing this, for example, it becomes possible to achieve a line cycle time of about 30 seconds.

And, according to another aspect of the present invention, a flaw inspection method which inspects for the presence of flaws on the surface of a workpiece includes: a step of measuring the surface position of an inspection region of the workpiece in a direction perpendicular to a predetermined rotational axis, for each rotational angle around the rotational axis; a step of acquiring, from the surface position for each rotational angle which has been measured, surface waveform data which specifies the waveform of the surface position with respect to rotational angle; a step of extracting, from the surface waveform data, high frequency waveform data which has a frequency higher than a predetermined frequency, or high frequency waveform data which specifies a change of a position within an angular range smaller than a predetermined angle; and a step of deciding upon the presence or absence of a flaw at the inspection region, based upon the high frequency waveform data which has been extracted.

According to the present invention, it is possible automatically to inspect for the presence of minute flaws upon the surface of a workpiece.

EMBODIMENT

In the following an embodiment of the device for inspecting for flaws in a workpiece surface will be explained with reference to the drawings. The embodiment explained hereinafter is a device for inspecting for the presence of flaws in the surface of a journal portion or of a pin portion of a crank shaft. However, it must be understood that it would also be easy for a person skilled in the art to be able, based upon the explanation of this inspection device for a crank shaft, to implement the present invention as an inspection device for a cam shaft, or for various other types of workpiece.

Figure 1:
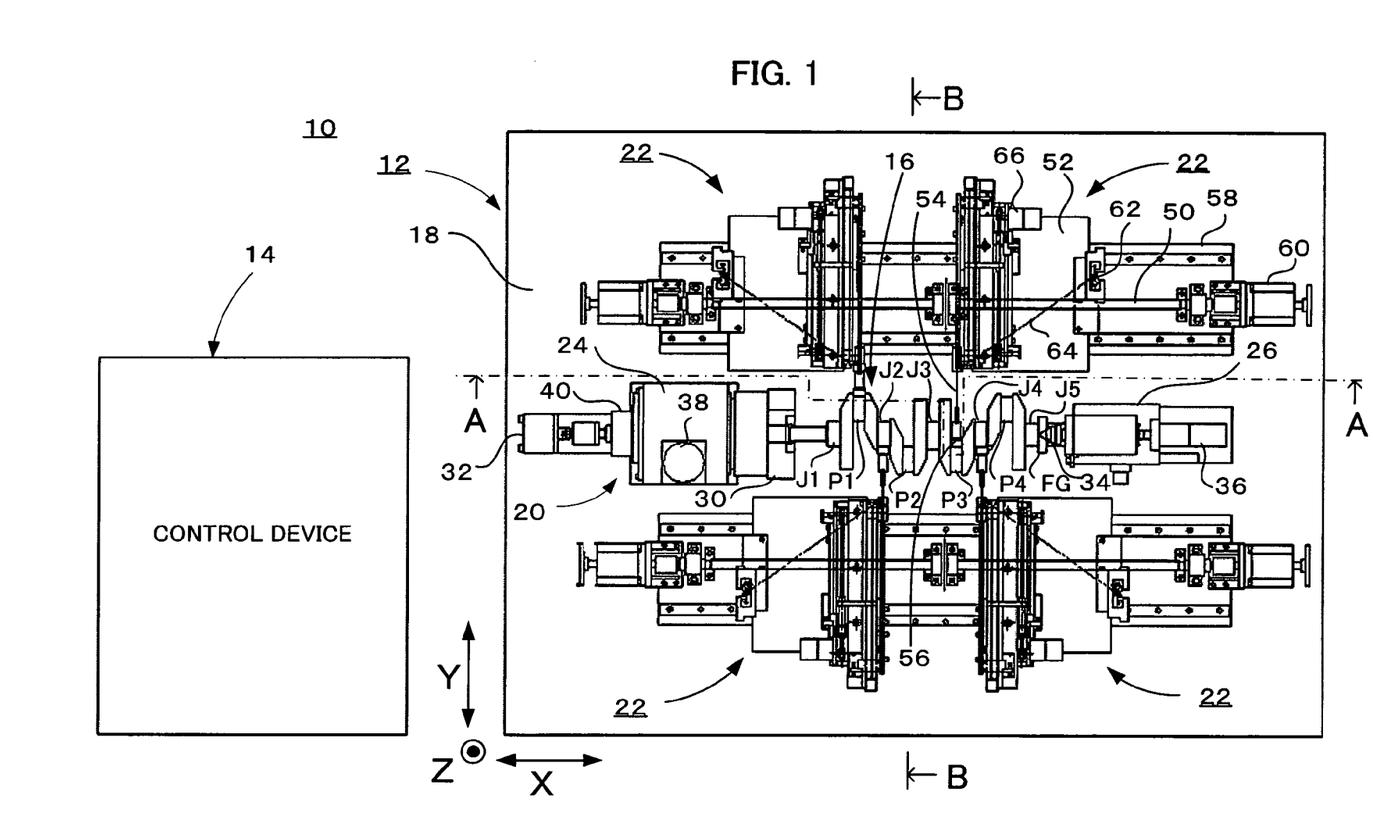
FIG. 1 is a plan view of an inspection device 10 according to an embodiment of the present invention.

FIG. 1 is a plan view of an inspection device according to this embodiment. In the following explanation, for the ease of comprehension, orthogonal X, Y, and Z axes are defined virtually, as shown in the figure.

As shown in FIG. 1, this inspection device 10 comprises a main device 12 and a control device 14 which is connected to the main device 12. The main device 12 is a machine which, while disposing a crank shaft 16 (which is the workpiece) so that its rotational axis is parallel to the X axis and rotating it about this rotational axis, automatically measures, for each rotational angle, the position in the Y axis direction of the outer circumferential surface of a journal portion or a pin portion of the crank shaft 16 (for example, this may be the position thereof taking the rotational axis as an origin, hereinafter termed the surface position), and outputs surface position data for each rotational angle. And the control device 14 comprises a personal computer, input and output boards, a communication interface board, a sequencer, and other control devices (these are not shown in the figures), and, along with controlling the operation of the main device 12 by software which is loaded upon the personal computer, by reading in, recording, and analyzing the above described surface position data from the main device 12, automatically detects the presence of flaws upon the outer circumferential surface of the journal portion or the pin portion of the crank shaft 16, and outputs the result of this decision.

As shown in FIG. 1, the main device 12 comprises a base stand 18, and a work operation unit 20 is installed in a central position upon this base stand 18, parallel to the X axis. Moreover, on the two flanks of this work operation unit 20, there are installed a plurality (for example, four) of contour measuring units 22. Among these, two of the contour measurement units 22, 22 are disposed upon one side of the work operation unit 20, while the other two thereof are disposed upon the opposite side of the work operation unit. These four contour measurement units 22, 22, 22, 22 have a mutually linearly symmetrical positional relationship as shown in the figure, and all have the same structure.

The work operation unit 20 supports the crank shaft 16 at both its ends so that the rotational axis of the crank shaft 16 is parallel to the X axis, and rotates the crank shaft 16 at a constant speed around this rotational axis, while moreover outputting encoder pulses corresponding to the rotational angle thereof. The calculation of the above described rotational angle is performed based upon these encoder pulses. Each one of the contour measurement units 22, 22, 22, 22 outputs encoder pulses according to the position in the Y axis direction of the outer subject of that journal portion or of that pin portion of the crank shaft 16 rotating upon the work operation unit 20, which is its inspection subject. Based upon these encoder pulses, the surface position of the journal portion or the pin portion which is the inspection subject (i.e. the position of the outer surface thereof in the Y axis direction) is calculated.

Although the interior of the base stand 18 is not shown in the figures, it contains a power supply circuit for the work operation unit 20 and the contour measurement units 22, 22, 22, 22, driver circuits which drive the work operation unit 20 and the contour measurement units 22, 22, 22, 22 according to control commands from the control device 14, a data processing circuit (the reference numeral 48 in FIG. 2) which inputs encoder pulses from the work operation unit 20 and the contour measurement units 22, 22, 22, 22, and calculates surface positions for each rotational angle and transmits them to the control device 14, and the like.

Figure 2:
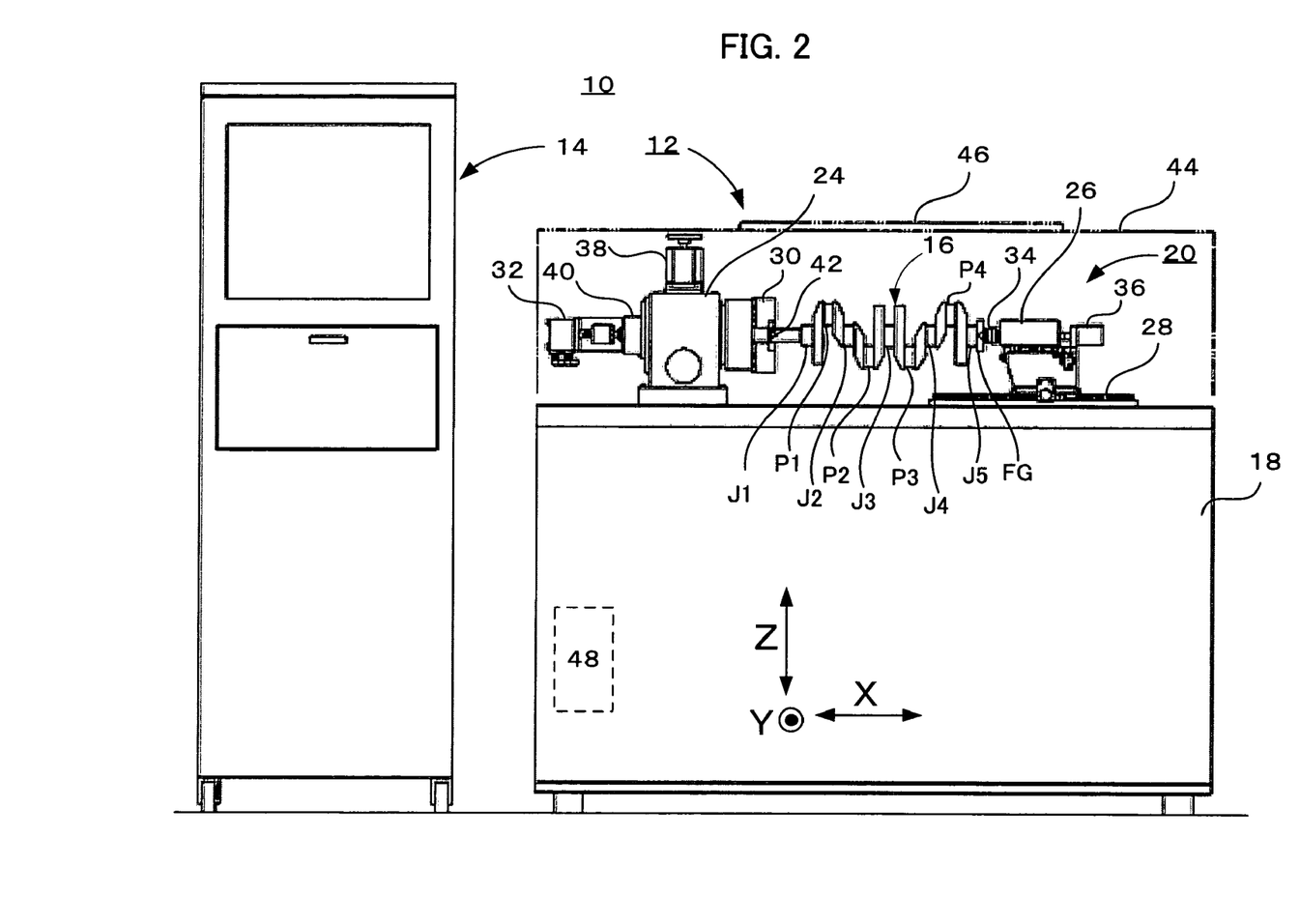
FIG. 2 is an elevation view of this inspection device 10, in which a work operation unit 20 upon a base stand 18 is shown more clearly by omitting from the drawing contour measurement units 22, 22.
Figure 3:
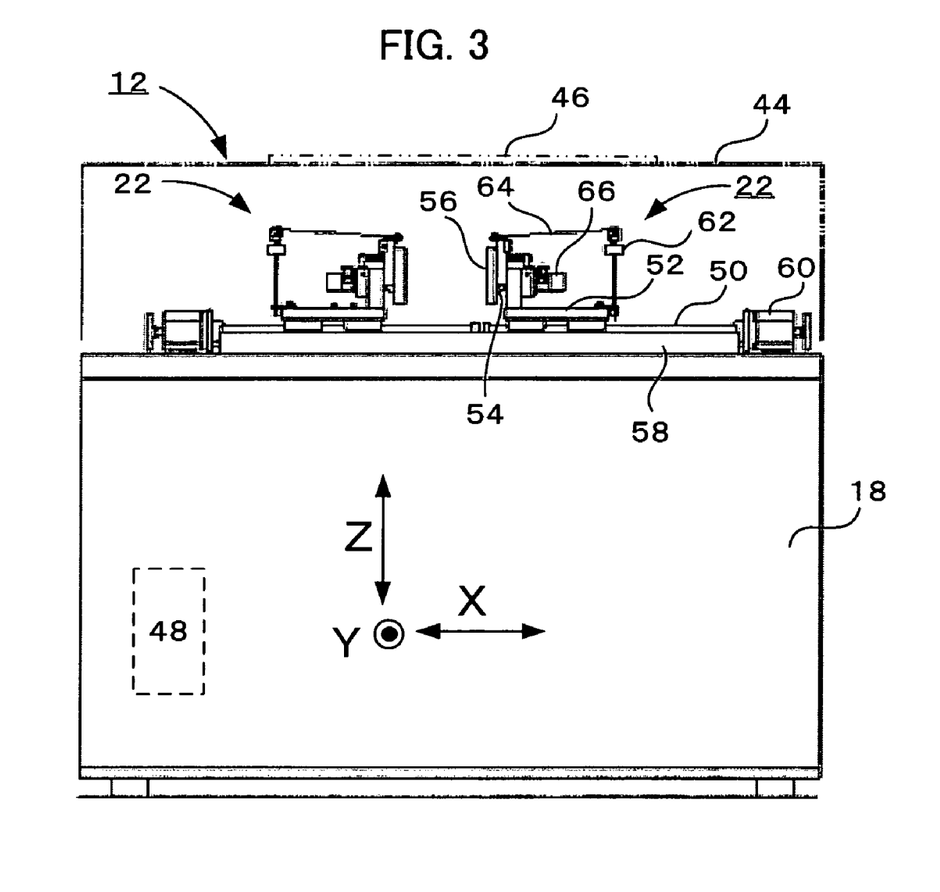
FIG. 3 is an elevation view as seen along a line A-A in FIG. 1, showing two contour measurement units 22, 22 which are positioned upon one side of the work operation unit 20.
Figure 4:
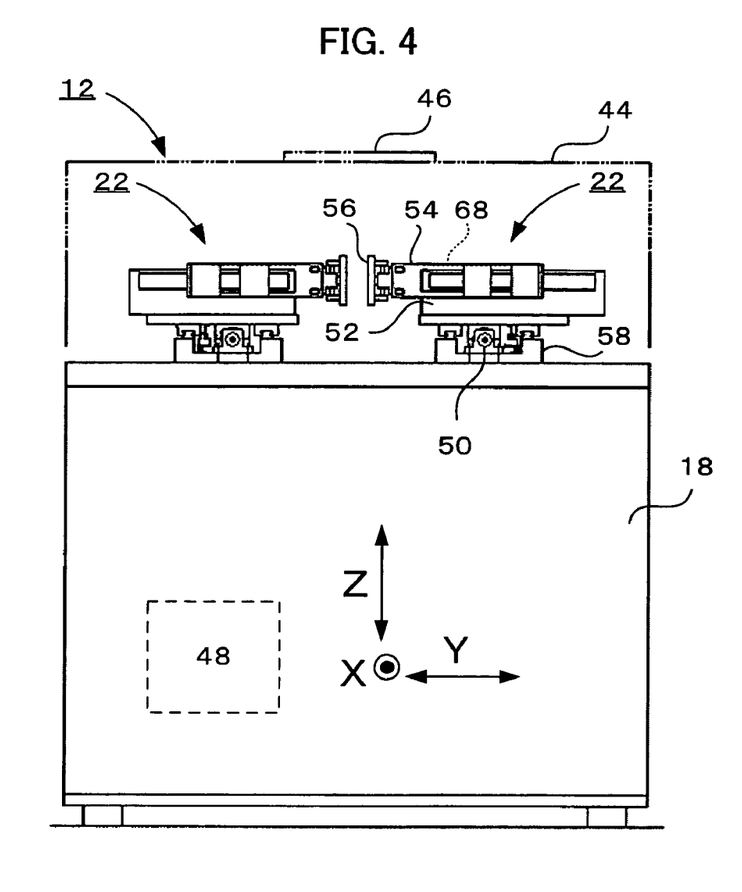
FIG. 4 is a side sectional view as seen along a line B-B in FIG. 1, showing two contour measurement units 22, 22 which are positioned upon both sides of the work operation unit 20.

FIG. 2 is an elevation view of this inspection device 10, and shows the work operation unit 20 upon the base stand 18 more clearly by omitting the contour measurement units 22, 22 from the drawing. FIG. 3 is an elevation view as seen along a line A-A in FIG. 1, showing two of the contour measurement units 22, 22 which are positioned upon one side of the work operation unit 20. And FIG. 4 is a side sectional view as seen along a line B-B in FIG. 1, showing two of the contour measurement units 22, 22 which are positioned upon both sides of the work operation unit 20.

In the following, the work operation unit 20 and the contour measurement units 22, 22, 22, 22 will be explained in more detail with reference to FIGS. 1 through 4.

As shown in FIGS. 1 and 2, the work operation unit 20 comprises a main shaft unit 24 and a tail stock 26. The tail stock 26 comprises a tail stock slide 28 for varying its position in the X axis direction. The distance from the main shaft unit 24 to the tail stock 26 can be set appropriately with this tail stock slide 28, according to the length of the crank shaft 16.

The main shaft unit 24 comprises a chuck 30 for gripping one end of the crank shaft 16. This chuck 30 can be driven to open and close by the operation of an air pressure driven chuck clamp cylinder 32. A chuck center 42 is provided at the center of the chuck 30. The tail stock 26 comprises a tail stock center 34 for supporting the other end of the crank shaft 16. This tail stock center 34 can be moved forward and backward by the operation of an air pressure driven tail stock cylinder 36. The tail stock center 34 is coupled to the tail stock cylinder 36 via a spring (not shown in the drawings), and, by the operation of this spring, it is possible to press the workpiece, i.e. the crank shaft 16, towards the chuck 30 with a constant force such that no bending of the crank shaft 16 takes place. It should be understood that the reference numeral 44 in the figure denotes a cover for preventing ingress of dust or the like, while the reference numeral 46 is an automatic door which is provided to an aperture in the cover 44 for bringing in and taking out the workpiece.

When the crank shaft 16 has been brought in on a temporary support (not shown in the drawings) disposed between the chuck 30 and the tail stock center 34, then the tail stock center 34 is brought forward and cooperates with the chuck center 42 so as to perform centering of the crank shaft 16. And the chuck 30 is closed so as to grasp one end of the crank shaft 16. The tail stock center 34 supports the other end of the crank shaft 16. Thereafter, a main shaft rotation motor 38 which consists of a stepping motor or a servo motor mounted to the main shaft unit 24 is started, and rotates the chuck 30 at a constant speed. Due to this, the crank shaft 16 rotates around its rotational axis at a constant speed. A precision rotary encoder 40 which is mounted to the main shaft unit 24 outputs encoder pulses at steps separated by a very minute rotational angle (for example at steps of 0.01 degrees), and, by inputting and counting these encoder pulses, the data processing circuit 48 within the base stand 10 detects the rotational angle of the crank shaft 16 at high accuracy.

As shown in FIGS. 1, 3, and 4, each one of the contour measurement units 22 comprises a table slider 50, a gauge head table 52, a gauge head slider 54, and a gauge head 56. The table slider 50 is a ball screw mechanism which is rotatably fixed upon the slide base 58, and which is driven by a table shift motor 60 which consists of a stepping motor or a servo motor. The gauge head table 52 is mounted upon the table slider 50. Due to the operation of the table slider 50, the gauge head table 52 can be shifted over a fixed range in the X axis direction. The position of the gauge head table 52 in the X axis direction is set variably according to the position of the journal portion or the pin portion of the crank shaft 16 which is the inspection subject. The position of the gauge head table 52 is detected based upon pulses from an internal encoder provided within the table shift motor 60, or from an externally provided encoder. The positions of the four contour measurement units 22, 22, 22, 22 in the X axis direction can each be set independently.

The gauge head slider 54 is installed upon the gauge head table 52, and the gauge head 56 is fitted to the end of the gauge head slider 54. This gauge head slider 54 is driven by a gauge head shift motor 66 which is a stepping motor or a servo motor, and thereby it is possible for the gauge head 56 to be moved forward or backward along the Y axis direction. By moving the gauge head 56 forward, the gauge head 56 comes to be contacted against the external circumference of the journal portion or the pin portion of the crank shaft 16 which is the inspection subject. The approach speed of the gauge head 56 to the crank shaft 16 directly before it contacts thereagainst is controlled to a low speed which will not create any flaws in the crank shaft 16. In the state in which the gauge head 56 is contacted against the crank shaft 16, the gauge head slider 54 is subjected, by an anchor 62 which is coupled thereto by a cord 64, to a pressure force in the forward direction (the direction for it to press against the crank shaft 16) of the minimum limit which is necessary for maintaining this contacting state between the gauge head 56 and the crank shaft 16. Due to this, while the crank shaft 16 rotates, the gauge head 56 is moved forward and backward in the Y axis direction according to the fidelity of the external diametrical shape of the crank shaft 16, while being kept in its state of contacting against the crank shaft 16. Furthermore, the gauge head 56 is also prevented from bending the crank shaft 16 and from causing flaws thereupon.

A precision linear encoder 68 (see FIG. 4) which is linked to the gauge head slider 54 outputs encoder pulses in very minute displacement steps according to the displacement of the gauge head 56 in the Y axis direction. By inputting and counting these encoder pulses, the data processing circuit 48 within the base stand 10 calculates at high accuracy the position of the gauge head 56 in the Y axis direction, in other words the surface position of the journal portion or the pin portion which is the inspection subject (i.e. the position of its outer surface in the Y axis direction). This surface position data which has thus been calculated is recorded by the data processing circuit and transmitted to the control device 14 together with the rotational angle data which has been detected simultaneously therewith.

The four contour measurement units 22, 22, 22, 22 independently measure the surface positions of four different journal portions or pin portions of the crank shaft 16 at the same time. For example, in the example shown in FIG. 1, measurement of the two journal portions J2 and J4, and of the two pin portions P1 and P3, is performed simultaneously.

Figure 5:
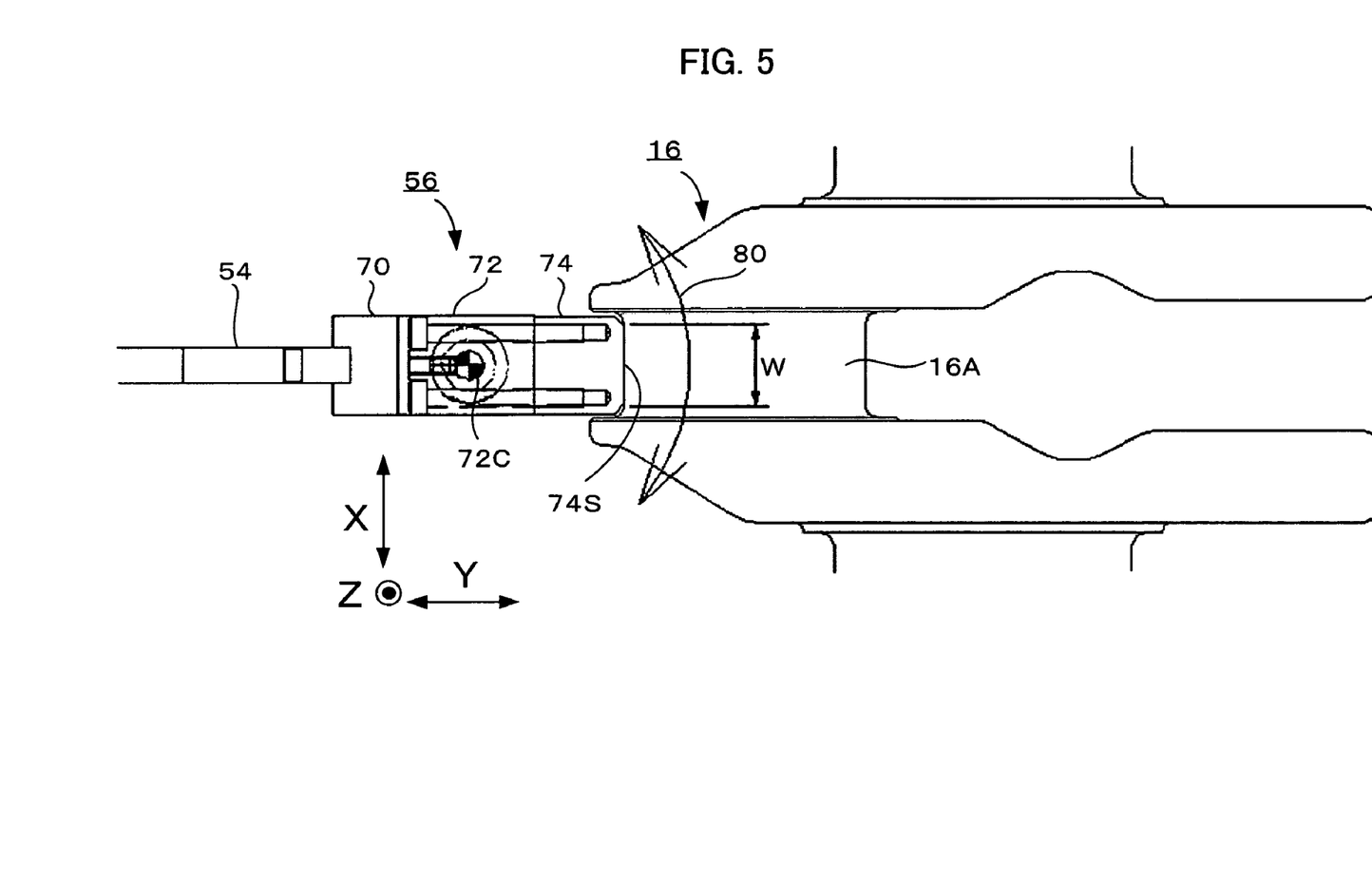
FIG. 5 is a plan view of a gauge head 56 in a state in which it is contacted against some pin portion P of a crank shaft 16.
Figure 6A:
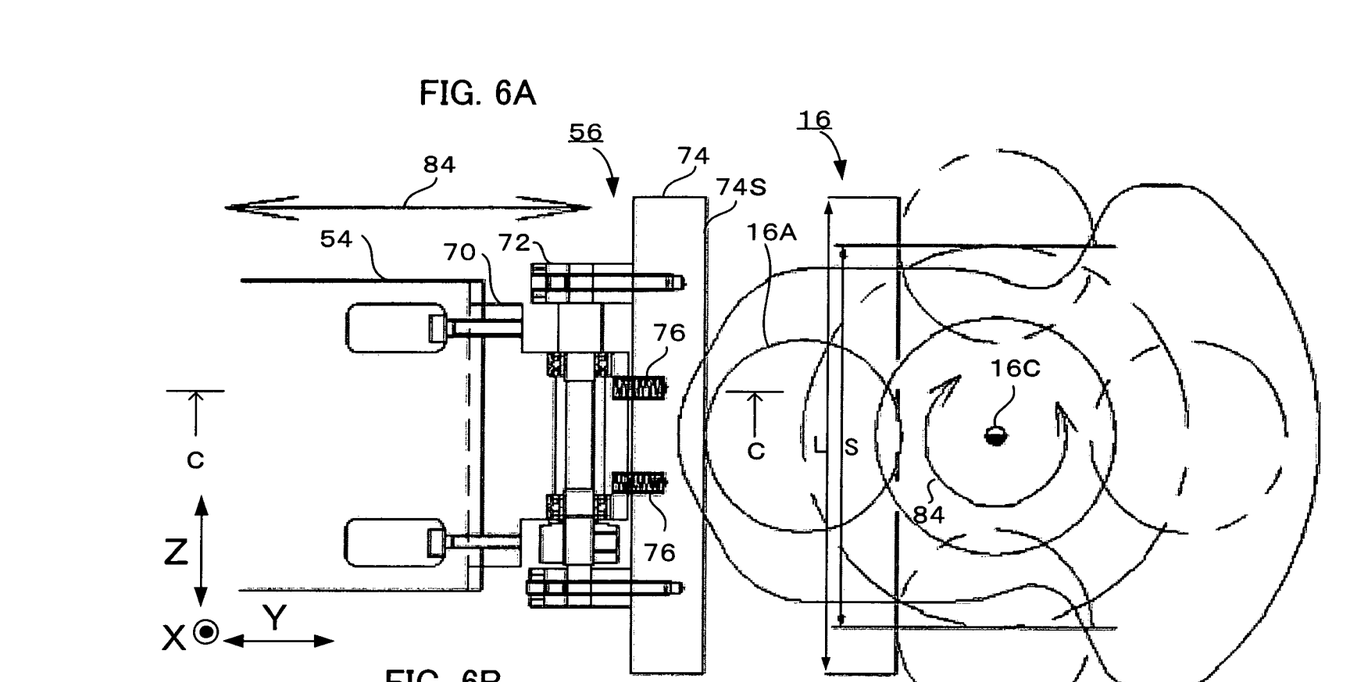
FIG. 6A is a side sectional view of the gauge head 56 in the same state.
Figure 6B:
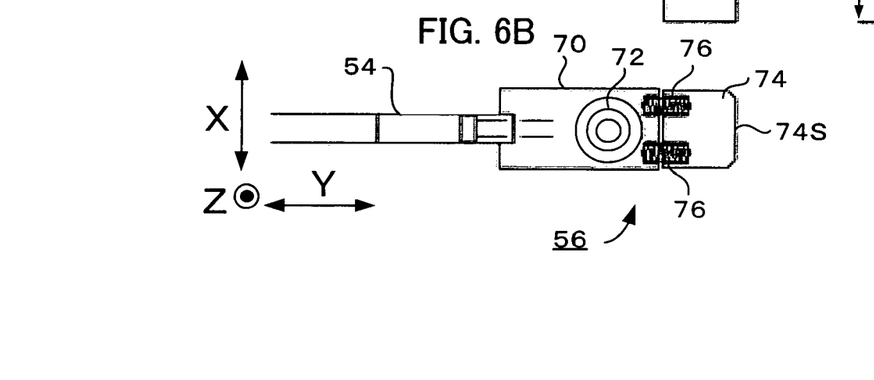
FIG. 6B is a plane sectional view of the gauge head 56 along a line C-C in FIG. 6A.
Figure 7:
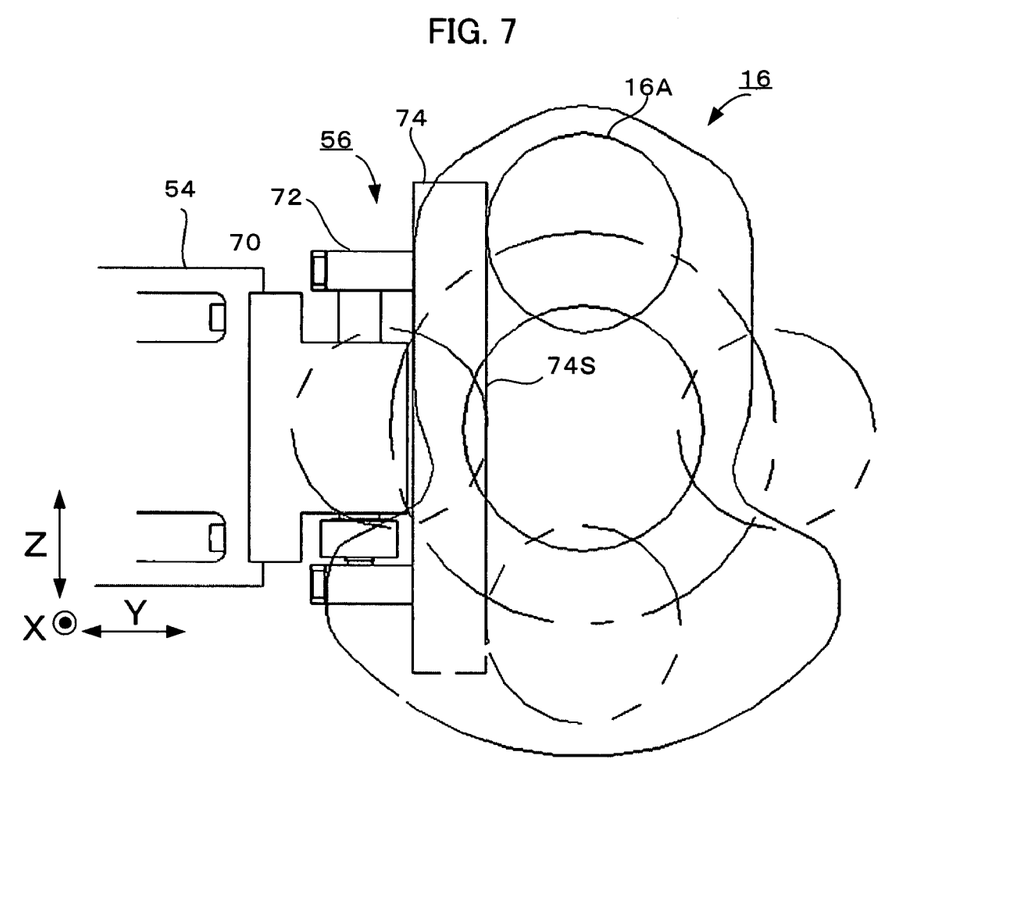
FIG. 7 is a side view of the gauge head 56 in a state in which the crank shaft 16 has been rotated through 90 degrees from its state shown in FIGS. 5 and 6A.

FIG. 5 is a plan view of the gauge head 56 in a state in which it is contacted against some inspection region (a pin portion or a journal portion) of the crank shaft 16 (here the state is shown, by way of example, in which it is contacted against a pin portion). FIG. 6A is a side sectional view of the gauge head 56 in the same state (FIG. 6A), and FIG. 6B is a plane sectional view of the gauge head 56 along a line C-C in FIG. 6A. And FIG. 7 is a side view of the gauge head 56 in a state in which the crank shaft 16 has been rotated through 90 degrees from its state shown in FIGS. 5 and 6A. As shown in FIGS. 5 through 7, the gauge head 56 comprises a head support member 70 which is fixed to the end of the gauge head slider 54, swing arms 72 which are fitted in bearings provided to the head support member 70 so as to rotate freely, and a head 74 which is fixed to the ends of the swing arms 72.

The gauge head 56 is capable of moving forwards and backwards along the Y axis direction due to the operation of the gauge head slider 54 which has already been explained, and thereby is subjected to pressure in the direction to press upon the inspection region 16A (the pin portion or the journal portion) of the crank shaft 16. The front end of the head 74 of the gauge head 56 has a contacting surface 74S which contacts against the outer surface of this inspection region 16A (the pin portion or the journal portion) of the crank shaft 16. This contacting surface 74S of the head 74 is a flat plane which has been processed to a high accuracy equal to or greater than that of the outer surface of the inspection region 16A, and which is parallel to the Z axis. As will be understood from FIGS. 6 and 7, the contacting surface 74S of the head 74 has a length L in the Z axis direction which is greater than or equal to the stroke length S in the Z axis direction of the inspection region (in particular, of the pin portion) 16A when the crank shaft 16 rotates. Due to this, the contacting surface 74S of the head 74 is always contacted against the inspection region 16A while the crank shaft 16 is rotating. Furthermore, as shown in FIG. 5, the contacting surface 74S of the head 74 has a dimension in the X axis direction (i.e. a width) which almost corresponds to (precisely, which is smaller by only a slight clearance than) the dimension (i.e. the width) in the X axis direction of the linear portion of the outer surface of the inspection region described above; and accordingly, when the crank shaft 16 rotates, this contacting surface comes to contact over the entire area of the outer surface of the inspection region 16A. Due to this, in one rotation of the crank shaft 16, it is possible to detect convex flaws which are present anywhere upon the outer surface of the above described inspection region, without overlooking any thereof.

As a variant embodiment, it would also be acceptable to arrange for the contacting surface 74S of the head 74 to have a width which almost corresponds to the minimum width among the widths which correspond to the linear portions in the X axis direction of the inspection regions 16A. And it would also be acceptable to arrange to perform the detection of flaws upon inspection regions of many types of widths with a head 74 of one and the same small width by, each time the crank shaft 16 is rotated, shifting the gauge head 56 in the X axis direction by just a distance less than or equal to the width of its contacting surface in the rotational axis direction.

The swing arms 72 for the gauge head 56 can swing through a fixed angular range around a rotational axis 72C along the Z axis direction, as shown by the arrow sign 80 in FIG. 5, and thereby the head 74 can be swung through the same range. Due to this swing function, the contacting surface 74S of the head 74 is always contacted against the outer surface of the inspection region 16A over its entire width, irrespective of bending errors in the crank shaft 16 and of parallelism errors of the outer surface of the inspection region 16A with respect to the rotational axis. And, because of this, it becomes possible to detect flaws at high accuracy.

Furthermore, the head 74 of the gauge head 56 is elastically pressed forward by a plurality of springs 76 (for example, by four thereof) which are fitted in the front end of the head support member 70, and there able more than required. Due to this, when the head 74 approaches the inspection region 16A, the clearance between the cheek portions of the inspection region 16A in both sides in the widthwise direction and the head 74 is only slight, and the head 74 is able to arrive at the inspection region 16A without contacting against its cheek portions.

The operation of the inspection device 10 having the structure described above is as follows (referring principally to FIGS. 1 and 2).

(1) The automatic door 46 at the upper portion of the main device 12 is opened, and a crank shaft 16, which is the workpiece, is loaded upon the workpiece temporary support (not shown in the drawings) by, for example, an auto loader, between the chuck 30 of the work operation unit 20 and the tail stock 26, and then the automatic door 46 is closed.

(2) The tail stock center 34 is forwarded by operation of the tail stock cylinder 36, and performs centering of the crank shaft 16 in cooperation with the chuck center 42. And the chuck 30 grasps the crank shaft 16 securely.

(3) Simultaneously with the above described grasping operation of the chuck 30, the positions of the contour measurement units 22, 22, 22, 22 in the X axis direction are adjusted by their table sliders 50, so that each of their gauge heads 56 is positioned to the position in the X axis direction of its respective one of the four inspection regions of the crank shaft 16 (i.e. in the example shown in FIG. 1, to the pin portions P1 and P3, and to the journal portions J1 and J4).

(4) Thereafter, each of the gauge heads 56 of the contour measurement units 22, 22, 22, 22 is forwarded, so that it contacts against the outer surface of its inspection region (i.e. its respective pin portion or journal portion).

(5) In the state in which all of the gauge heads 56, 56, 56, 56 are contacted against their respective inspection regions, the crank shaft 16 is rotated, and the data processing circuit 48 receives the encoder pulses from the rotary encoder 40 and the linear encoders 68 (FIG. 4), and calculates the position of each of the gauge heads 56 (the surface position of each inspection region) for each rotational angle, for example rotational angles at a spacing of 0.01 degrees. The rotational angle data and the surface position data which have been calculated are transmitted to the control device 14 and recorded.

(6) After the rotation of the crank shaft 16 has been completed, all of the gauge heads 56, 56, 56, 56 are withdrawn. Next, by steps the same as (3) to (5) described above, using the four contour measurement units 22, 22, 22, 22, the surface positions of four other inspection regions upon the crank shaft 16 (for example, the pin portions P2 and P4 and the journal portions J2 and J5) are measured for each rotational angle. And next, by the same steps, using the four contour measurement units 22, 22, 22, 22, the surface positions of the remaining two inspection regions upon the crank shaft 16 (for example, the journal portion J3 and the flange portion FG) are measured. In the case of this crank shaft 16 for a four cylinder engine which is shown by way of example in FIGS. 1 and 2, by the three rotations above, measurement is completed for the surface positions of all of the inspection regions P1~P4, J1~J5, and FG. In this connection, if the inspecting is completed in three rotations in this manner, it is possible to achieve a process cycle time of about 30 seconds.

(7) The control device 14 analyzes the surface position data of each detection location for each rotational angle which have thus been recorded, decides whether any flaw is present upon the outer surface of each detection location, and outputs the results of these decisions.

The function and the operation of the control device 14 for performing the data analysis and decision mentioned in (7) above will now be explained in detail in the following.

It is considered that, apart from the flaw data which is the object of detection, errors due to the following causes may be included in the surface position data which has been measured upon an inspection region in which a flaw has occurred:

(1) Shape errors due to processing errors by the processing machine;

(2) Errors of planarity of the contacting surface 74S of the head 74 of the gauge head 56;

(3) Errors of the straightness of the contacting surface 74S of the head 74 of the gauge head 56 in the X axis direction and the Z axis direction;

(4) Errors in the flatness and the straightness in the X axis direction of the outer surface of the inspection region; and (5) Errors due to eccentricity of the inspection region from the rotational axis.

When the waveform which expresses change of the surface position data with respect to rotational angle is considered, all of the errors (1) through (4) described above are generally thought to lie in the waveform components of low frequency which are included in this waveform. In consideration of this fact, by eliminating from the waveform described above the low frequency waveform component in which it is considered that the errors described above are contained, the control device 14 extracts the high frequency waveform component which it is considered specifies the flaw data which is in practice the objective of inspecting. And the control device 14 decides upon the presence or the absence of flaws based upon the gradient or the amplitude or the like of the high frequency waveform component which has thus been extracted.

As techniques for eliminating the above described low frequency component, the control device may employ either of the techniques (A) and (B) described below.

(A) The low frequency waveform data is extracted from the surface position waveform data including the above errors (1) through (4) which is obtained from the surface position data for each rotational angle which has been measured (hereinafter termed the "original data") by eliminating the high frequency component by averaging filtering. And the high frequency waveform data is then extracted by subtracting this low frequency waveform data which has thus been extracted by averaging filtering from the original data.

(B) The original data is expanded in Fourier series, and the low frequency waveform data is obtained by extracting only the low order components from this Fourier series. And the high frequency waveform data is then extracted by subtracting this low frequency waveform data from the original data.

Figure 8:
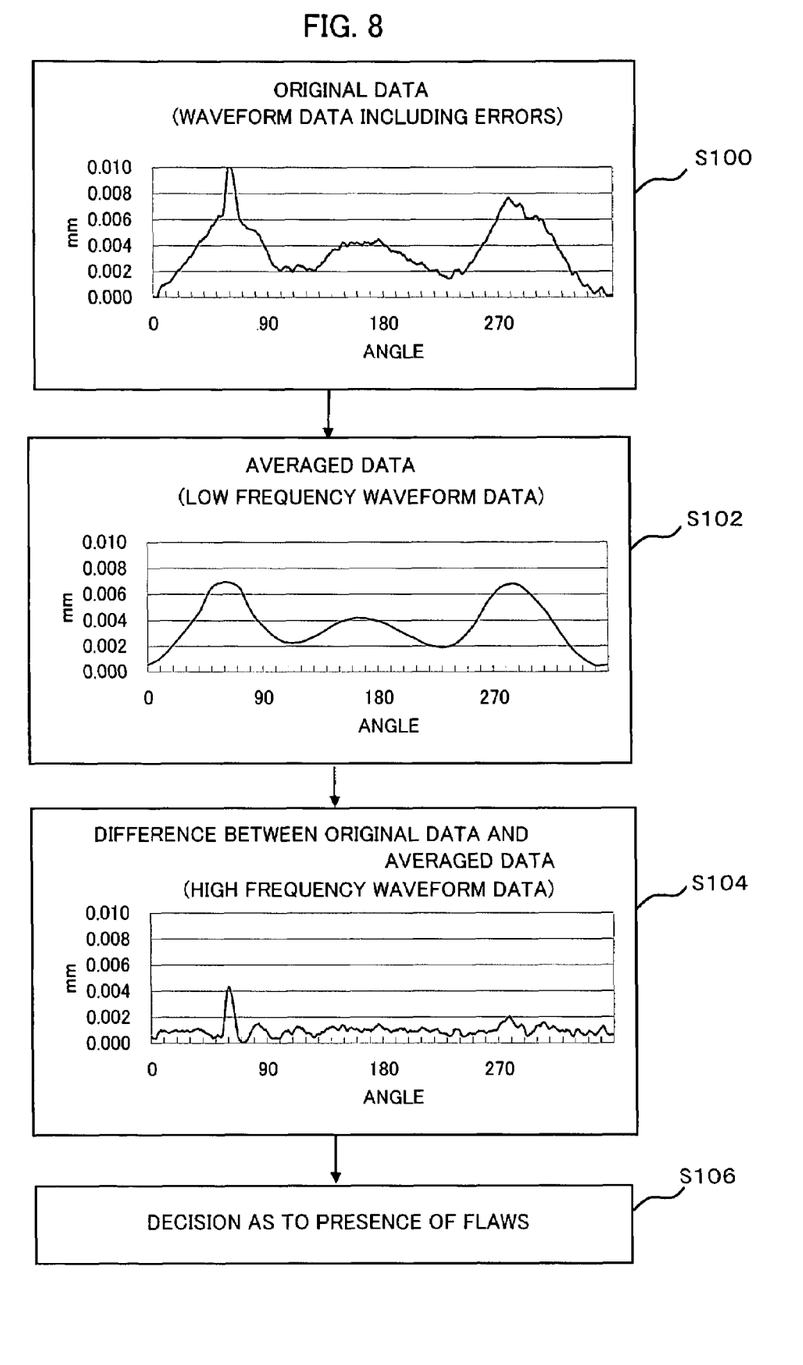
FIG. 8 is a flow chart showing successive stages of a data processing procedure by a control device 14 using averaging filtering.

FIG. 8 is a flow chart showing successive stages of a data processing procedure in which the averaging filtering of technique (A) described above is used.

In a step S100 of FIG. 8, by arranging the surface position data for each rotational angle in one rotation which have been measured in sequence of rotational angle, the control device 14 generates original data which shows the changing waveform at the surface position with respect to rotational angle, as shown in the block for the step S100 in the figure. At this time it would also be acceptable, in order to alleviate the burden of the data processing, to perform averaging for each angular range of 1 degree upon the surface position data which has been measured for each rotational angle at steps of, for example, 0.01 degrees, thus converting this data into surface position data at rotational angle steps of 1 degree, and to use this as the original data.

And, in a step S102, this original data is averaged over some constant range of rotational angle, for example 30 degrees. In other words, if as described above, for example, the original data consists of an array of surface position data in rotational angle steps of 1 degree, then, for each rotational angle in rotational angle steps of 1 degree, the surface position data items over a range 15 degrees to left and right thereof, i.e. over a total rotational angle range of 30 degrees centered upon this rotational angle (i.e. a total of 31 items of surface position data), are read out from the original data, the average value of these 31 items of surface position data is calculated, and the surface position data item at that rotational angle is replaced by this average value. This replacement by the average value of the data over 30 degrees is performed for each item of surface position data over the entire surface position data rotational angle range from 0 to 359 degrees. By doing this, as shown in the block for the step S102, averaged data values are obtained by averaging over the range of 30 degrees. This averaged data is low frequency waveform data which includes only the low frequency component, which is the component of change of the surface position over a large angular range greater than or equal to 30 degrees. And, although this averaged data includes components due to the errors (1) through (4) described above, it is considered that it does not include any fine component (i.e. any high frequency component) of surface position change due to flawing. In this connection, according to experiments performed by the present inventors, as a rotational angle range for averaging, the value of 30 degrees described above by way of example is an appropriate value for eliminating the components due to the errors (1) through (4) described above.

And, in a step S104, the averaged data is subtracted from the original data. By doing this, as shown in the block for this step S104, high frequency waveform data is obtained which includes only the high frequency component, which is the component of surface position change within a small angular range of less than 30 degrees. In this high frequency waveform data, there is included any fine surface position change component (i.e. any high frequency component) due to flawing.

And, in a step S106, the presence or absence of flaws is decided upon based upon the gradient or the amplitude or the like of the high frequency waveform data. To put it in another manner, based upon the high frequency waveform data, the height or the width or the like of a portion at which the rate of change of the surface position with respect to rotational angle (i.e. the gradient) and/or the surface position has changed with respect to rotational angle is obtained, and convex flaws in the pin portion or the journal portion are detected by comparing this with a threshold value which is set in advance. For example, 0.003 mm may be set as the threshold value for the amount of change of surface position per 1 degree of rotational angle displacement (i.e. gradient), and, if it has been discovered that a gradient greater than or equal to this threshold value is included in the high frequency waveform data, then it may be decided that a flow is present within this portion. Or, this decision may be performed with the amount of change (i.e. gradient) per 0.1 degrees, and by doing this it may be anticipated that detection can be performed with higher accuracy. Furthermore, according to requirements, it is also possible to calculate the portions for which the surface position changes with respect to rotational angle based upon peaks or valleys in the high frequency waveform data, to compare the amplitude (the height) or the width thereof with a predetermined threshold value, and to decide upon the presence or absence of flaws by also using this comparison result as material for the decision.

Figure 9:
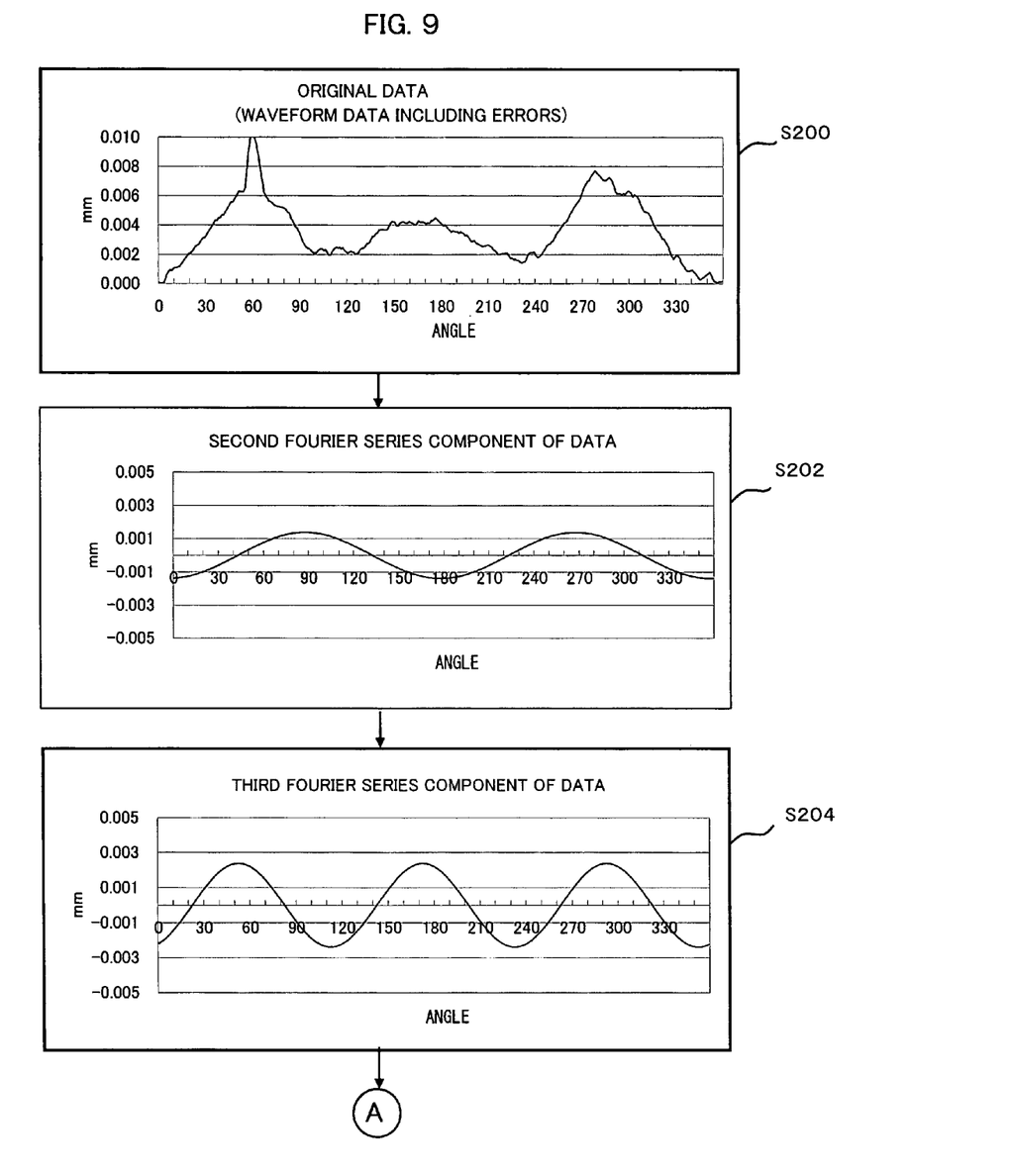
FIG. 9 is a flow chart showing successive stages of a data processing procedure by the control device 14 using Fourier expansion.
Figure 10:
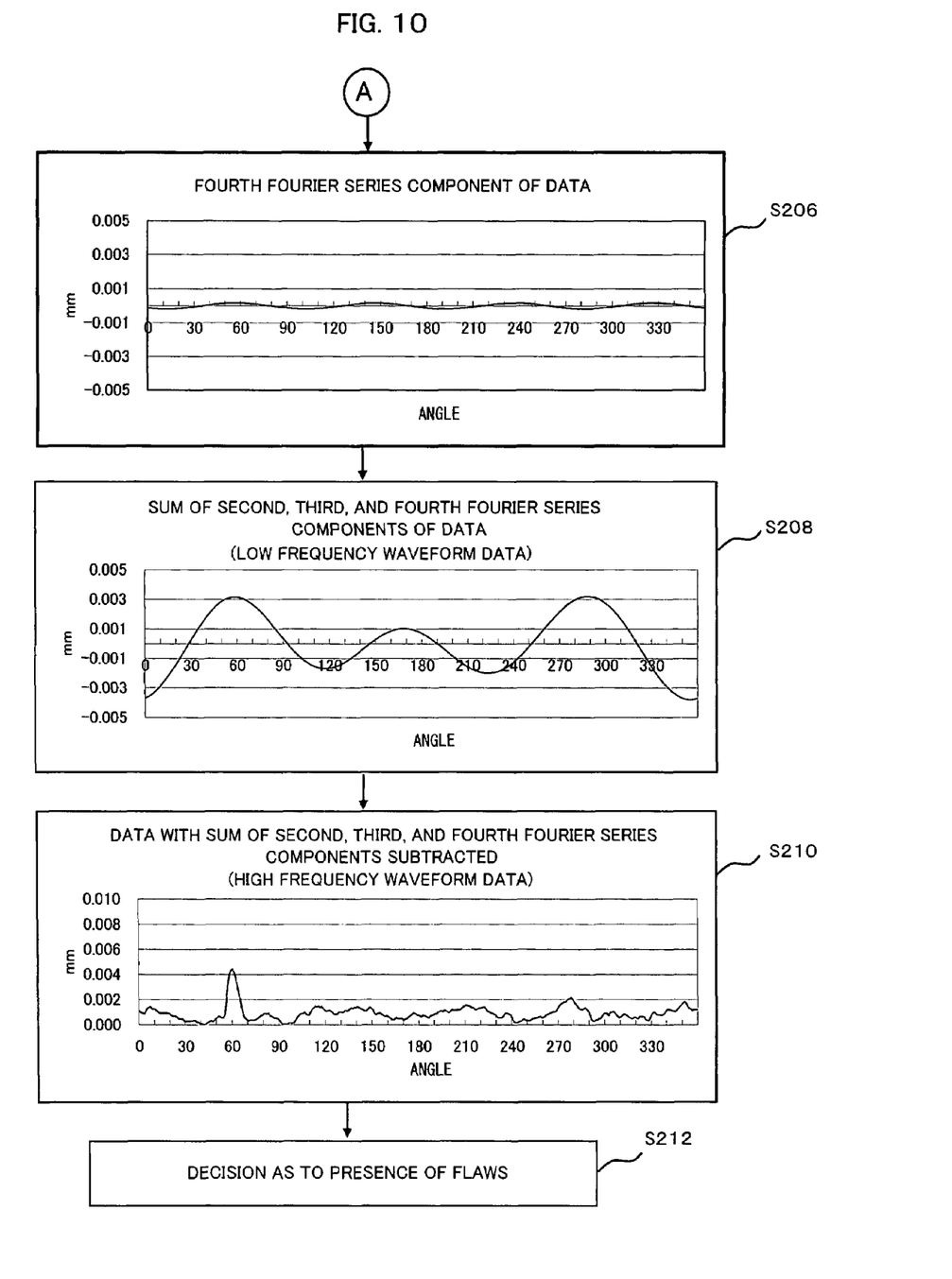
FIG. 10 is a continuation of the flow chart of FIG. 9.

FIG. 9 and FIG. 10 are flow charts showing successive stages of a data processing procedure in which the Fourier expansion of technique (B) described above is used.

In a step S200 of FIG. 9, the original data is obtained as already explained. In the step S202 of FIG. 9 through the step S206 of FIG. 10, the waveform of the original data is expanded in the form of Fourier series, thus:

$$F(t)=a_0/2+a_1 \cos(t)+a_2 \cos(2t)+\ldots+a_n \cos(nt)+\ldots+_1 \sin(t)+_2 \sin(2t)+\ldots+_n \sin(nt)+\ldots$$

And, in the subsequent step S208, in order to obtain the low frequency waveform data, the Fourier coefficients in a required low order range are obtained: for example, in the case of the range from the primary coefficient to the fourth order coefficient, the Fourier coefficients $a_0$, $a_1$, $a_2$, $a_3$, $a_4$, $_{0, 1, 2, 3}$, and $_4$ are obtained. And, as shown in the blocks for the steps S202 through S206, the waveform data for each order in this low order range are obtained from these Fourier coefficients $a_0$, $a_1$, $a_2$, $a_3$, $a_4$, $_{0, 1, 2, 3}$, and $_4$.

And, in a step S208, waveform data is obtained by adding together the waveform data up to the above described low order range, for example from the primary to the fourth order. This waveform data is low frequency waveform data which includes only the low frequency components up to the fourth order from the original data. And, although this low frequency waveform data includes components due to the errors (1) through (4) described above, it is considered that it does not include any fine component (i.e. any high frequency component) of surface position change due to flawing. In this connection, according to experiments performed by the present inventors, as a range for the low frequency data to be obtained, the range of up to the fourth order shown above by way of example, or at the very most the range up to the sixth order, is appropriate from the point of view of eliminating the components due to the errors (1) through (4) described above.

And, in a step S210, this low frequency waveform data is subtracted from the original data. By doing this, as shown in the block for this step S210, high frequency waveform data is obtained which includes only the high frequency component, which is the fine component of surface position change of the fifth order and above. In this high frequency waveform data, there is included any fine surface position change component (i.e. any high frequency component) due to flawing.

And, in a step S212, the presence or absence of flaws is decided upon based upon the gradient or the amplitude or the like of the high frequency waveform data. The method for decision here is the same as in the step S106 of FIG. 8.

The data processing of the above described FIG. 8 or FIGS. 9 and 10 may be executed by a computer according to software, or may be executed by dedicated wired hardware, or also may be executed by a combination thereof.

Although an embodiment of the present invention has been explained above, this embodiment is only given by way of example in order to explain the present invention; the scope of the present invention is not intended to be limited only to this embodiment. The present invention may also be implemented in various other kinds of modes, provided that its gist is not departed from.

The invention claimed is:

1. A flaw inspection device, which inspects for presence of a flaw on a surface of a workpiece, comprising:
    a surface position measurement device that, while rotating said workpiece around a predetermined rotational axis, measures a surface position of an inspection region of said workpiece in a direction perpendicular to said rotational axis, with respect to angular position of the workpiece about the rotational axis;
    a surface waveform acquisition means which receives an output signal of said surface position measurement means and acquires surface waveform data, which specifies said surface position with respect to the angular position of the workpiece;
    a high frequency waveform extraction means, which extracts, from said surface waveform data, high frequency waveform data that has a frequency higher than a predetermined frequency or high frequency waveform data that specifies a change of a position within an angular range smaller than a predetermined angle; and
    a flaw decision means that determines whether a flaw exists at said inspection region, based upon said extracted high frequency waveform data.

2. The flaw inspection device described in claim 1, wherein:
    said surface position measurement device comprises a gauge head that is adapted to contact a surface of the inspection region upon said workpiece, and said gauge head, along with shifting freely along a first direction, which is orthogonal to the rotational axis of said workpiece, is also biased towards said workpiece, to continuously contact the inspection region of said workpiece while said workpiece is rotated; and
    said surface position measurement device measures the surface position of said inspection region with respect to the angular position of the workpiece, by measuring a position of said gauge head while said workpiece is rotated.

3. The flaw inspection device described in claim 2, wherein the contacting surface of said gauge head to said inspection region has a predetermined length in a second direction which is orthogonal to the shifting direction of said gauge head and to a direction of said rotational axis of said workpiece, and said predetermined length is equal to or greater than a stroke length of said inspection region in said second direction when said workpiece rotates.

4. The flaw inspection device described in claim 2, wherein the contacting surface of said gauge head to said inspection region is a flat plane which has been processed to an accuracy equal to or greater than that of the surface of said inspection region, and the contacting surface has a width in the direction of said rotational axis that is approximately the same as a width of said inspection region in the direction of said rotational axis.

5. The flaw inspection device described in claim 2, wherein the contacting surface of said gauge head to said inspection region has a width in the direction of said rotational axis that is approximately the same as a minimum width among widths of straight lime portions of said inspection regions in the direction of said rotational axis.

6. The flaw inspection device described in claim 2, wherein said gauge head can swing within a predetermined angular range round, as a center, a rotational axis in a second direction which is orthogonal to a direction of said rotational axis of said workpiece and to said shift direction of said gauge head.

7. The flaw inspection device described in claim 2, wherein:
said gauge head comprises a head having a contacting surface for contacting said inspection region
said head is constructed to swing within a predetermined angular range around, as a center, a swing axis in a direction that is orthogonal to a shift direction of said gauge and to the rotational axis of said workpiece; and
said swing axis is positioned farther than said contacting surface from said workpiece in the shift direction of said gauge.

8. The flaw inspection device described in claim 2, wherein:
said gauge head comprises a head having a contacting surface for contacting said inspection region;
said head can swing within a predetermined angular range around, as a center, a rotational axis in a direction which is orthogonal to a shift direction of said gauge and to the rotational axis of said workpiece; and
said head is elastically biased so that said contacting surface is parallel to the rotational axis of said workpiece in natural condition in which no external force is applied.

9. The flaw inspection device described in claim 1, wherein, based upon said high frequency waveform data, said flaw decision means calculates a rate of change with respect to the rotational angle of the surface position of said inspection region, and detects a flawing in said inspection region by comparing said rate of the change which has been calculated with a threshold value set in advance.

10. The flaw inspection device described in claim 1, wherein, based upon said high frequency waveform data, said flaw decision means obtains a height or a width of portions at which the surface position of said inspection region changes with respect to the rotational angle, and detects a flaw in said inspection region by comparing said height or width with a threshold value set in advance.

11. The flaw inspection device described in claim 1, wherein said surface position measurement device is part of a contour measurement unit, and the contour measurement unit is one of a plurality of contour measurement units whose relative positions with respect to said workpiece are variable, and said contour measurement units simultaneously measure surface positions of different inspection regions upon the same workpiece independently.

12. The flaw inspection device described in claim 1, wherein the surface waveform data represents the surface characteristics of the workpiece throughout a 360° rotation of the workpiece, and the surface waveform data includes low frequency components, which have a frequency below the predetermined frequency, and high frequency components, which have a frequency higher than the predetermined frequency, and the high frequency waveform data represents only the high frequency components, and the flaws that are determined by the flaw decision means are indicated only by characteristics of the high frequency components.

13. The flaw inspection device described in claim 1, wherein the surface position measurement device is adapted to engage the inspection region while the workpiece rotates.

14. The flaw inspection device described in claim 1, wherein said flaw decision means acquires, as said high frequency waveform data, a difference between said surface waveform data and averaged data obtained by averaging said surface waveform data within an angular range of 30 degrees.

15. The flaw inspection device described in claim 1. wherein said flaw decision means acquires, as said high frequency waveform data, a difference between said surface waveform data and the sum of order components not over a fourth order Fourier series of said surface waveform data.

16. A flaw inspection device which inspects for presence of a flaw on a surface of a workpiece comprising:
a surface position measurement device which, while rotating said workpiece around a predetermined rotational axis, measures a surface position of an inspection region of said workpiece in a direction perpendicular to said rotational axis with respect to angular position of the workpiece; and
a control device which is connected to said surface position measurement device, wherein said control device: receives an output signal of said surface position measurement device; acquires surface waveform data which specifies said surface position with respect to each of rotational angles; extracts, from said surface waveform data which has been acquired, high frequency waveform data which has a frequency higher than a predetermined frequency, or high frequency waveform data which specifies a change of a position within an angular range smaller than a predetermined angle; and decides upon the presence or absence of a flaw at said inspection region, based upon said high frequency waveform data which has been extracted.

17. A flaw inspection method which inspects for presence of a flaw on a surface of a workpiece, comprising:
a step of measuring a surface position of an inspection region of said workpiece in a direction perpendicular to a predetermined rotational axis, for each of rotational angles around said rotational axis;
a step of acquiring, from said surface position for each of the rotational angles which has been measured, surface waveform data which specifies a waveform of said surface position with respect to each of the rotational angles;
a step of extracting, from said surface waveform data, high frequency waveform data which has a frequency higher than a predetermined frequency, or high frequency waveform data which specifies a change of a position within an angular range smaller than a predetermined angle; and
a step of deciding upon the presence of a flaw at said inspection region, based upon said high frequency waveform data which has been extracted.

* * * * *